US006287251B1

(12) United States Patent
Tan

(10) Patent No.: US 6,287,251 B1
(45) Date of Patent: **\*Sep. 11, 2001**

(54) SPECULUM

(75) Inventor: Gary Gay Chee Tan, Osborne Park (AU)

(73) Assignee: MCA Medical Products Pty Ltd, Osborne Park (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/677,539

(22) Filed: Oct. 2, 2000

Related U.S. Application Data

(63) Continuation of application No. 09/381,017, filed as application No. PCT/AU98/00737 on Sep. 14, 1998, now Pat. No. 6,174,282.

(30) Foreign Application Priority Data

Sep. 9, 1997 (AU) .................................................. PO 9067

(51) Int. Cl.$^7$ ........................................................ A61B 1/00
(52) U.S. Cl. ............................................................ 600/224
(58) Field of Search ..................................... 600/219, 220, 600/224

(56) References Cited

U.S. PATENT DOCUMENTS

| 52,014 | 1/1866 | Barlett . |
| 380,745 | 4/1888 | Chamberlin . |
| 1,614,065 | 1/1927 | Guttmann . |
| 3,817,242 | 6/1974 | Uddenberg . |
| 4,385,626 | * 5/1983 | Danz ................................... 600/220 |
| 5,377,667 | 1/1995 | Patton et al. . |
| 5,509,893 | * 4/1996 | Pracas ................................ 600/224 |
| 5,916,151 | 6/1999 | Charters . |

FOREIGN PATENT DOCUMENTS

| 2698778 | 6/1994 | (FR) . |
| 2054 | 1/1884 | (GB) . |
| 43218 | 1/1982 | (GB) . |
| 288157 | 10/1988 | (GB) . |
| WO 92/21279 | 12/1992 | (WO) . |
| WO 94/12091 | 6/1994 | (WO) . |

* cited by examiner

Primary Examiner—Gene Mancene
Assistant Examiner—Edvando C. Robert
(74) Attorney, Agent, or Firm—Workman, Nydegger & Seeley

(57) ABSTRACT

A speculum 10 includes a main body 12 with two dialator fingers 14A and 14B that are connected at their respective proximal ends 16A and 16B to the main body 12. A further dialator finger 28 extends between the fingers 14A and 14B and is fixed to the main body 12. An actuator 20 is pivotally coupled to the main body 12. The actuator 20 is formed with a dialator finger 70 that is located between the fingers 14A and 14B and opposite the fixed finger 28. When the actuator 20 is pivoted the finger 70 immediately commences to pivot away from the remaining fingers 14 and 28. After a predetermined degree of pivot, the actuator 20 comes into contact with the inside of fingers 14 near their approximal ends 16 to cause the distal ends of those fingers to move away from each other. Fingers 14A and 14B are hinged about respective canted hinge axis so that when they are abutted by the actuator 20 they move in a combined upward and sideways motion.

13 Claims, 4 Drawing Sheets

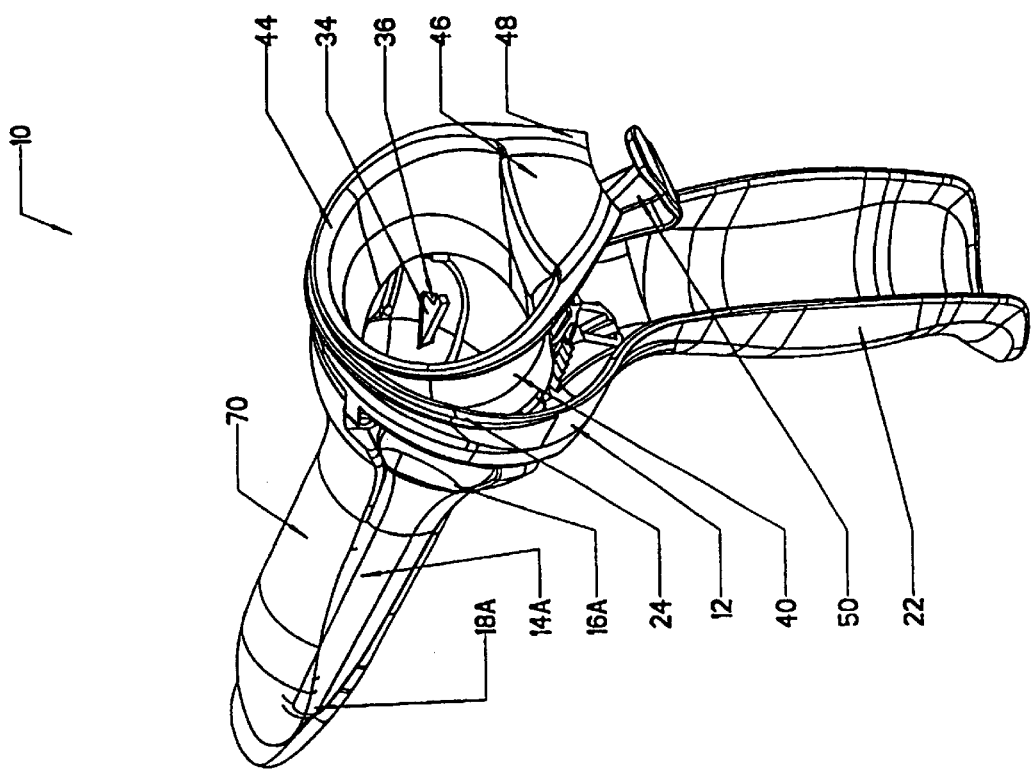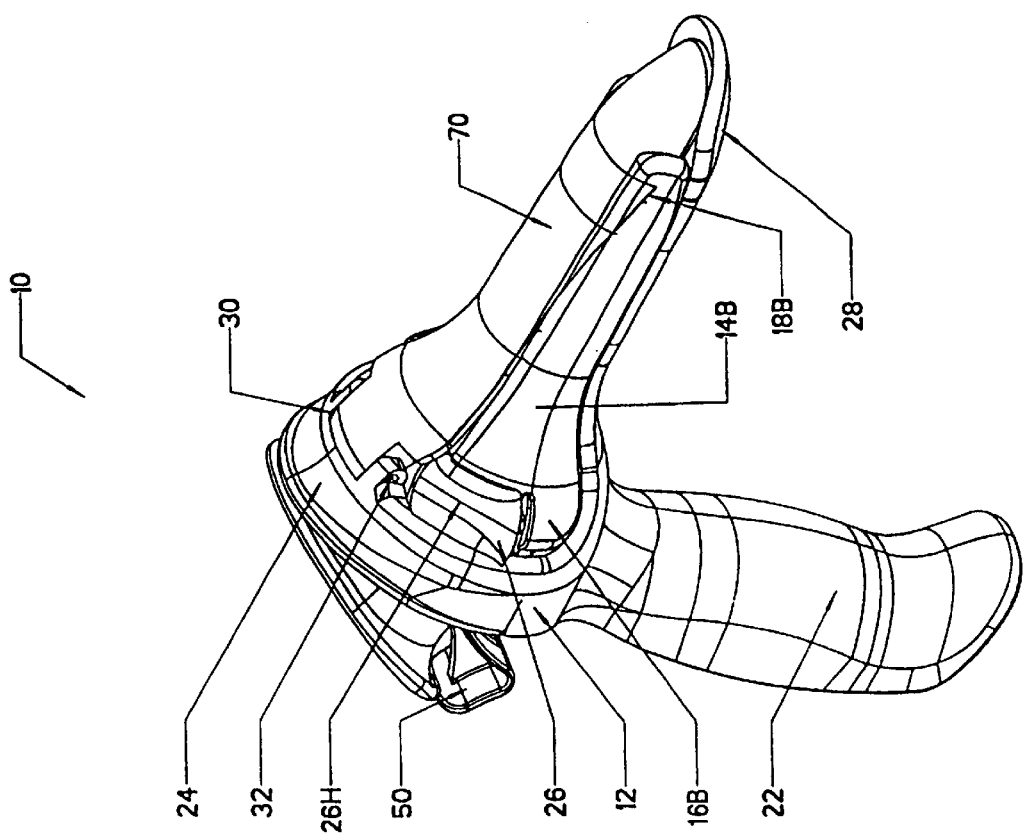

SPECULUM

RELATED APPLICATION

This application is a continuation of U.S. patent application Ser. No. 09/381,017, filed Sep. 14, 1999, for "Speculum," U.S. Pat. No. 6,174,282, which is a U.S. nationalization of International Application No. PCT/AU98/00737, filed Sep. 9, 1998.

FIELD OF THE INVENTION

This invention relates to a speculum for dilating, visualising and instrumenting a body cavity such as a vagina or rectum.

BACKGROUND OF THE INVENTION

A conventional speculum comprises a plurality of dilator members or arms which are spread by an actuator for enlarging a body cavity. There are commonly two types of actuators, the lever type and the cam or iris type. The lever type actuator typically comprises a pair of handles each having one dilator arm arranged in a manner so that when the handles arc squeezed together the dilator arms spread apart. An inherent drawback with most lever type speculums is that the levers or handles are disposed in the line of sight of the body cavity therefore obscuring a view of the cavity under examination and/or interfering with the placement of medical instruments.

In the iris type speculums, the dilator arms are moved outwardly in a spiralling motion. As a result, the arms must slide against the tissue in the cavity being examined which may cause pinching of the tissue or discomfort to the patient. A further disadvantage with the known iris type speculums is their relatively complex construction and manufacture which increases costs to the extent that the speculums are in general, intended for multiple use. This therefore necessitates a strict hygiene and sterilisation program to ensure that there is no cross infection between patients. Accordingly, the use of iris type speculums is generally inconvenient to practitioners and increases the cost of service.

A further generation of speculums is known in which a rotating annular cam bears against the side of pivotal dilator arms causing the arms to pivot outwardly. An example of such a speculum is shown in Applicant's International application no. PCT/AU96/00125 (WO 96/28083). While this type of speculum has several advantages over the lever and iris type speculums described above, it is still relatively complex in manufacture requiring the production of numerous separate components which must then be assembled into the complete speculum.

SUMMARY OF THE INVENTION

It is an object of the present invention to provide a speculum which is inexpensive to manufacture and assemble and thus can be produced economically to facilitate once only disposable use and does not adversely affect visualisation or instrumenting of a body cavity.

According to the present invention there is provided a speculum body for dilating a body cavity, said speculum including at least:

a main body;

a plurality of first dilator fingers, each of said first fingers having a proximal end and a distal end, said first dilator fingers hinged at their proximal ends to said main body about respective canted hinge axes to allow said first dilator fingers to move with a combined upward and sideways motion; and an actuator pivotally coupled to said main body so that said actuator can be pivoted into abutment with said first dilator fingers to cause said first dilator fingers to move outwardly with said combined upward and sideways motion thereby dilating said body cavity.

Preferably a short rib is provided on an inside surface adjacent said proximal end of each of said first dilator fingers, said rib being engaged by said actuator to effect said abutment of said actuator with said first dilator fingers.

Preferably each rib is provided with a recess for receiving said actuator when said actuator is pivoted into abutment with said first fingers.

Preferably said rib and said hinge axis of a corresponding first dilator finger are offset from each other in a direction transverse to a longitudinal axis of said corresponding finger.

Preferably said hinge axis and said rib of corresponding finger are disposed on opposite sides of said longitudinal axis of said corresponding finger.

Preferably said main body includes a first ring-like structure to which said first dilator fingers are hinged and said actuator comprises a second ring-like structure which pivots inside said first ring-like structure, said first and second ring-like structures defining a window through which said cavity can be viewed when said actuator is pivoted into abutment with said first dilator fingers.

Preferably the speculum further includes a second dilator finger located between adjacent first dilator fingers, said second dilator finger having a proximal end attached to said actuator, a distal end spaced from said proximal end, and opposite lateral edges extending between said proximal end and said distal end, said distal end of said second dilator finger extending beyond said distal end of said first dilator fingers.

Preferably the speculum further includes a third dilator finger coupled to said main body and located between adjacent first dilator fingers opposite said second dilator finger, said third dilator finger having a distal end that extends beyond said distal end of said first dilator fingers and said distal end of said second dilator finger.

Preferably said third dilator finger is coupled by an integral hinge to said main body.

Preferably said actuator pivots through a first angle prior to abutment with said first dilator fingers so that said second finger commences to move before said first dilator fingers.

Preferably the speculum further includes a releasable locking mechanism for locking said fingers in a desired juxtaposition and subsequently releasing said fingers.

Preferably said releasable locking mechanism includes a first component provided on said actuator and a second component provided on said main body, said first and second components arranged to engage each other when said actuator is pushed in a direction of insertion of said speculum into said body cavity, and released from each other when a force is applied to said actuator to a direction oblique to said direction of insertion.

Preferably said first component comprises one of a pawl and a rack of teeth-like projections, and the second component comprises the other of the pawl and the rack, said pawl and rack being biased into engagement when said actuator is pushed in said direction of insertion, and lifted apart to effect disengagement when said force is applied.

BRIEF DESCRIPTION OF THE DRAWINGS

An embodiment of the present invention will now be described by way of example only, with reference to the accompanying drawings in which:

FIG. 1 is a perspective view from the front of a speculum in accordance with a first embodiment of the present invention;

FIG. 2 is a perspective view of the speculum shown in FIG. 1 from the rear;

DETAILED DESCRIPTION OF THE PREFERRED EMBODIMENT

Figure 5:
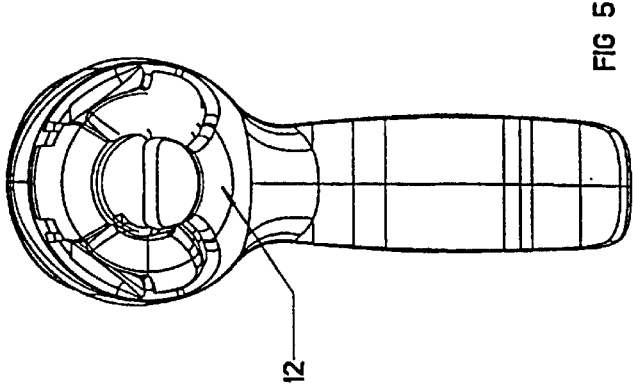
FIG. 5 is a front end view of the speculum.
Figure 4:
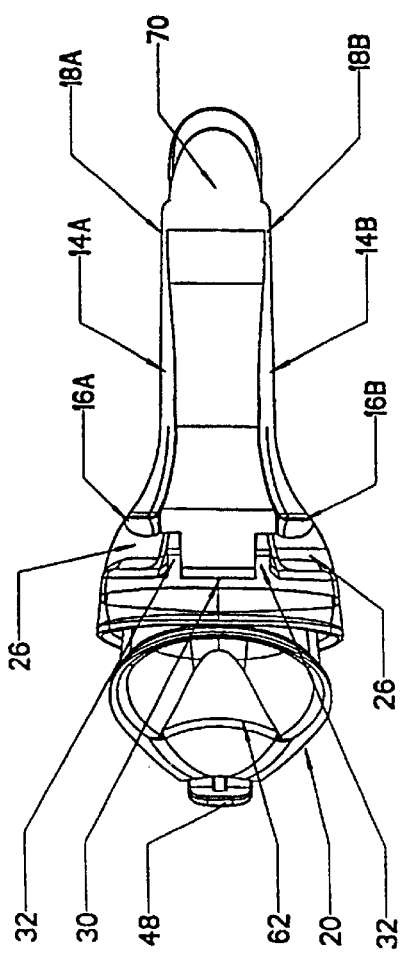
FIG. 4 is a top view of the speculum.
Figure 3:
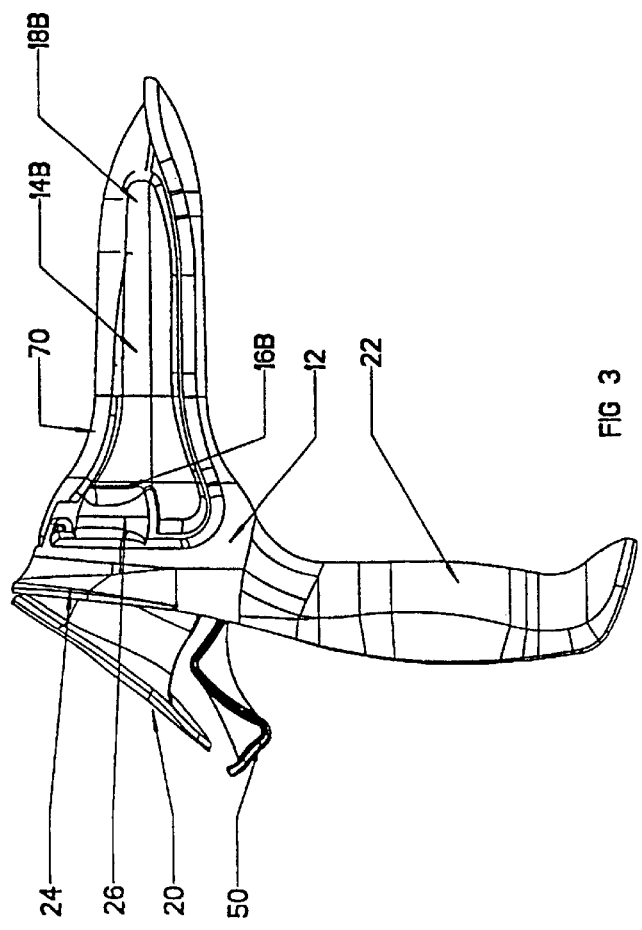
FIG. 3 is a side view of the speculum.

The speculum 10 comprises a main body 12 and a plurality (in this instance two) first dilator fingers 14A and 14B (hereinafter referred to collectively as "fingers 14"), which are each connected at their respective proximal ends 16A and 16B to the main body 12. The coupling of the fingers 14 to the main body 12 is in a manner so that the fingers 14 and in particular their respective distal ends 18A and 18B can move away from each other when acted upon by actuator 20. The actuator 20 is pivotally coupled to the main body 12 so that when it is pushed in a direction of insertion of the speculum into the body cavity, the actuator pivots into abutment with the inside of the fingers 14 near their proximal ends 16 causing the distal ends 18 to move away from each other thereby dilating the body cavity.

The body 12 comprises a handle 22 which terminates at its upper end with a ring or annulus type structure 24. The fingers 14 are coupled to the structure 24 and extend in the axial direction of the structure 24 and generally perpendicularly to the handle 22. The fingers 14 are attached to the structure 24 by tabs which form hinges 26. Located between the lower longitudinal edges of fingers 14A and 14B is a further finger 28. The finger 28 is fixed to the ring like structure 24 and extends parallel to and beyond fingers 14. The main body 12, that is the handle 22, ring like structure 24, hinges 26 and fingers 14 and 28 are integrally formed as a single unit. As is evident from FIG. 1, each hinge 26 has a hinge axis 26H which is canted or inclined relative to its respective fingers 14 so that when fingers 14 move they move with a combined upwards and sideways motion. That is the hinge axis 26H about which a finger 14 moves extends along a tangent to ring like structure 24 but is inclined from the perpendicular to the longitudinal axis of that finger 14.

A rectangular cut-out 30 is formed on an upper part of the structure 24 between the fingers 14A and 14B. On each side of the cut-out 30 is an integrally formed detent 32. The detents 32 capture respective pins (not shown) formed on the actuator 20 to provide a snap-fit pivotal connection between the actuator 20 and the main body 12. The detents can be in the form of holes formed in lobes provided on opposite sides of the cut-out 30 for receiving the pins on the actuator 20.

A short rib 34 (see FIG. 2) is formed on the inside surface of each finger 14 adjacent its proximal end 16. The rib 34 extends in the direction of the length of its respective finger 14 and is provided at an end adjacent the ring structure 24 with a recess 36 at its proximal end. Each rib 34 is offset from the hinge 26 of its corresponding finger 14. Moreover, the hinge 26 and rib 34 of each finger 14 are spaced on opposite sides of longitudinal axis 38 of each finger 14, as seen most clearly in FIG. 6.

The actuator 20 also includes a ring like structure or shell 40 having an arcuate forward edge 42 and a rearward edge 44 which is also arcuate but inclined to the forward edge 42 so that the depth of the shell 40 generally increases from its top to its bottom. Extending rearwardly and downwardly from the bottom of the shell 40 is a thumb rest 46. The thumb rest 46 is in the form of a concave depression formed in a downwardly depending flange 48 integrally provided on the actuator 20.

Figure 6:
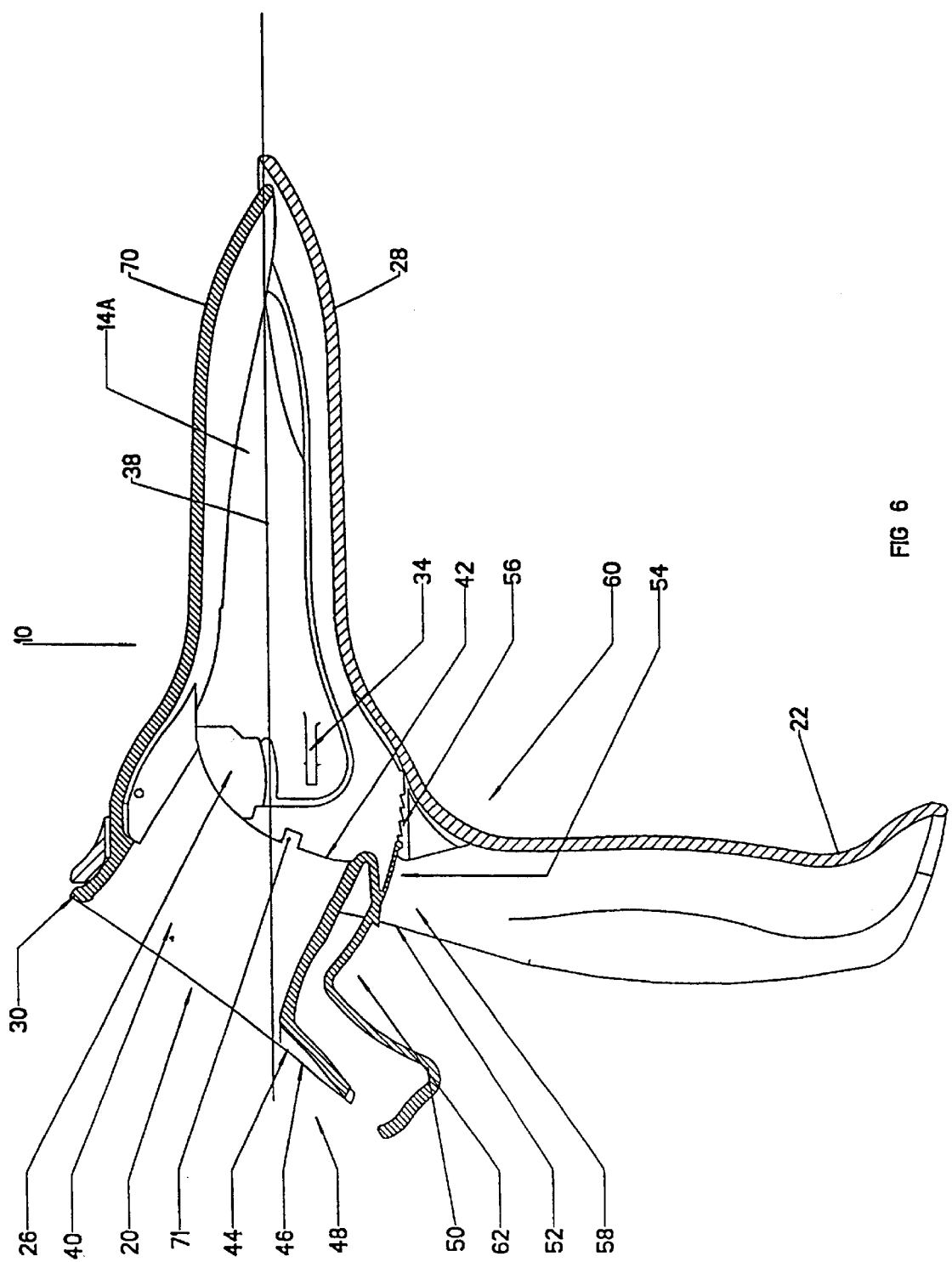
FIG. 6 is a sectional view of the speculum.

As best seen in FIG. 6, a releasable locking mechanism 52 is provided for locking the relative positions of the fingers so as to maintain a desired dilation of the body cavity and then allowing subsequent release of the fingers. The locking mechanism 52 comprises a first component in the form of a pawl 54 which is integrally formed with the actuator 20 and a rack 56 of teeth like projections formed on the inside of the ring like structure 24 and extending centrally along a length of the finger 28. The pawl 54 is part of a spring like thumb actuated release mechanism 50 that is integrally formed with forward edge 42 of the actuator 20 and extends rearwardly to a location adjacent the rearward edge 44.

The pawl 54 includes a tongue 58 that extends in the forward direction and disposed above the rack 56. The tongue 58 is biased so as to normally press on the rack 56. The forward most and rearward most ends of the tongue 58 are provided with a first barb 60 and second barb 62 respectively for engaging the rack 56. The barbs 60 and 62 are spaced so that the second barb 62 does not engage the rack 56 until the first barb has been pushed forward beyond the rack 56. Ideally the second barb 62 engages the rack 56 when the speculum is approximately half fully open. In this embodiment this corresponds roughly to the actuator 20 commencing to push against the inside of fingers 14. The shape and location of the second barb 62 provided for a greater bias against the rack 56 than the first barb 60.

The shape of the pawl 54, in combination with a nature of the material from which it is made and the juxtaposition of the actuator 20 to the main body 12 ensures that at all times at least one of the barbs 60, 62 are maintained in bias contact with the rack 56 when the actuator 20 is pivoted inwardly to spread the fingers of the speculum 10. The purpose of the first barb 60 is mainly to provide tactile feed back to the user rather than to firmly hold the fingers in position. It is the second barb 62 that enables the distal ends of the fingers to be held apart with incrementally increasing spread as it engages successive teeth along the rack 56.

To release the fingers, the release mechanism 50 is pushed upwardly. This lifts the second barb 62 out of engagement with the rack 56. By now also pushing backwardly the actuator can be pivoted back in a controlled manner to close the speculum 10. The first barb 60 can still lightly engage the rack 56 however its engagement force is easily overcome by the upward and backward thumb pressure applied to the mechanism 50.

Figure 7:
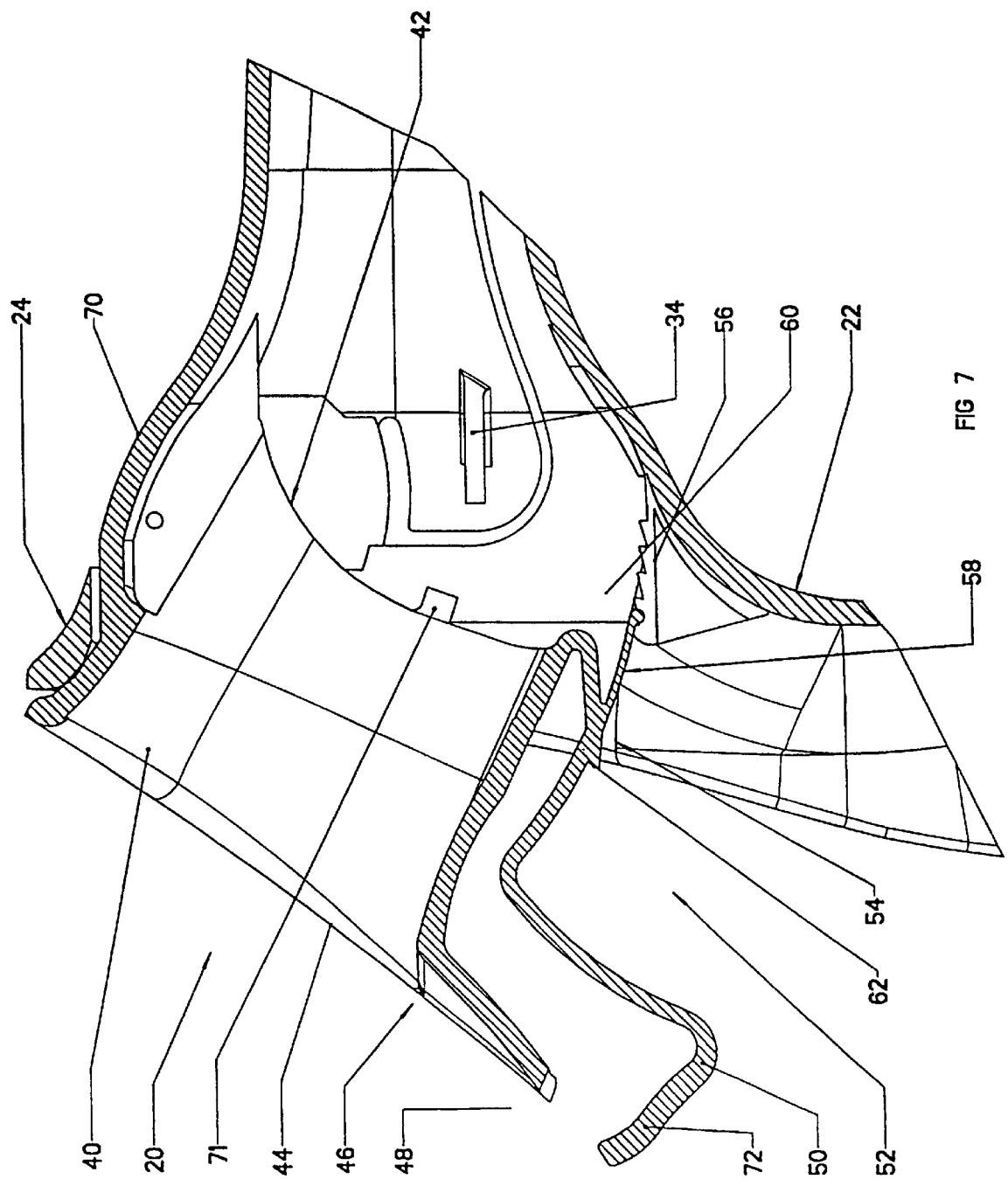
FIG. 7 is an enlarged sectional view of part of an actuator of the speculum shown in FIG. 6.

The actuator 20 is provided with an integral finger 70. The finger 70 extends from the forward edge 42 and is accommodated at its proximal end in the cut-out 30. The previously mentioned pins which are received in the detents 32 for pivotally coupling the actuator 20 to the main body 12, extend laterally from opposite sides of the proximal end of finger 70. The finger 70 is located between the upper longitudinal edges of fingers 14A and 14B, and is diametrically opposite the finger 28. The distal end of finger 70 together with the distal end of finger 28 form a duck bill like structure when the actuator 20 is in the free or closed state. In the embodiment shown, the distal end of the finger 28 extends beyond that of the finger 70. A locating lug 71 (see FIGS. 6 and 7) extends forward of edge 42 on opposite sides of the actuator 20 and sits slightly above the rib 34 when the edge 42 is received in the recess 36 of each rib 34.

The actuator 20 which includes the shell 40, thumb rest 46, mechanism 50, pawl 54, lugs 71 and finger 70 is made as a single integral component. Accordingly, the speculum 10 can be made from two separate components which can be easily and quickly constructed without the aid of any tools by pushing or otherwise locating the pins formed on the sides of the finger 70 into the detents 32.

In order to use the speculum 10, it is simply gripped by the handle 22 and slowly pushed into the cavity requiring dilation. With the thumb of the operator located in the thumb rest 46, the actuator 20 is pushed in the direction of insertion to cause the actuator 20 to pivot about the pins located in the detents 32. This pivoting motion results in the immediate pivoting of finger 70 so that its distal end moves away from the distal end of finger 28. While this occurs the barb 60 engages successive teeth on the rack 56 to provide tactile feedback of the motion of the finger 70. After a predetermined degree of pivoting of actuator 20, further pivoting results the barb 62 engaging the rack 56 and the forward edge 42 seating in recess 36 and bearing against the rib 34 on each of the fingers 14. As further thumb pressure is applied the actuator 20 continues to pivot which results in the fingers 14A and 14B moving about their respective hinges 26 so that their distal ends move away from each other. As the actuator 20 is pivoted, the second barb 62 engages successive teeth on the rack 56. At any time, if the thumb pressure is released once the barb 62 engages one of the teeth, the fingers 14, 70 and 28 are held in a fixed relationship to each other.

In order to allow the liners to collapse and pivot back toward each other, the mechanism 50 is pushed upwardly and backwardly resulting in a lifting of the pawl 54 thereby disengaging the barb 62 from the rack 56.

It will be appreciated that when in use, the cavity being dilated can be visualised Or instrumented through the shell 40 of the actuator 20 and ring like structure 24 of the main body 12. As the speculum 10 can be made from only two components and assembled in a matter of seconds without the aid of any tools, it can be manufactured at such a low cost that it can be used once and then disposed of. Further, the actuator 20 is only in abutment with the ends of fingers 14, therefore there is very little frictional engagement of the components of the speculum 10. This avoids the problem of the speculum "sticking open" due to high frictional forces when in use. This may occur for example with speculums in which an actuator pushes laterally against the inside surfaces of dilator fingers to cause them to spread. In the present speculum, the actuator only pushes against the proximal ends of the fingers, essentially in the direction of insertion of the speculum.

Now that an embodiment of this invention has been described in detail, it will be apparent to those skilled in the relevant arts that numerous modifications and variations may be made without departing from the basic inventive concepts. For example, the finger 28 is shown as being fixed to the main body 12 in a manner so that it does not pivot. However, it will be possible to construct the speculum 10 with the finger 28 supported by an integral hinge similar to hinges 26 so that it can be pivoted away from fingers 14 and 70. This will naturally require changes in the design of the actuator 20 so that it also abuts the distal end of the finger 28 to cause the pivoting motion. Further, the releasable locking mechanism 52 is not a critical part of the invention and can be dispensed with so that the fingers can be held apart by the maintaining of thumb pressure on the thumb rest 46.

The speculum 10 can also be provided with one or more stops to limit the pivoting motion of the actuator 20 and thus the degree of spread of the fingers 14, 28 and 70. In its simplest form this could be achieved by simply forming a stop bar or face on say the actuator 20 to come into contact with the main body 12 after a predetermined degree of pivoting with the actuator 20.

While the speculum 10 can be made from any material including stainless steel, it is preferred that it be made from a plastics material to facilitate low manufacturing cost and ease of construction.

All such modifications and variations are deemed to be within the scope of the present invention, the nature of which is to be determined from the foregoing description and the appended claims.

The claims defining the invention are as follows:

1. A speculum body for dilating a body cavity, said speculum including at least:

a main body;

a plurality of first dilator fingers, each of said first fingers having a proximal end and a distal end, said first dilator fingers hinged at their proximal ends to said main body about respective canted hinge axes to allow said first dilator fingers to move with a combined upward and sideways motion; and an actuator pivotally coupled to said main body so that said actuator can be pivoted into abutment with said first dilator fingers to cause said first dilator fingers to move outwardly with said combined upward and sideways motion thereby dilating said body cavity.

2. The speculum according to claim 1 wherein a short rib is provided on an inside surface adjacent said proximal end of each of said first dilator fingers, said rib being engaged by said actuator to effect said abutment of said actuator with said first dilator fingers.

3. The speculum according to claim 2 wherein each rib is provided with a recess for receiving said actuator when said actuator is pivoted into abutment with said first fingers.

4. The speculum according to claim 2 wherein said rib and said hinge axis of a corresponding first dilator finger are offset from each other in a direction transverse to a longitudinal axis of said corresponding finger.

5. The speculum according to claim 4 wherein said hinge axis and said rib of corresponding finger are disposed on opposite sides of said longitudinal axis of said corresponding finger.

6. The speculum according to claim 1 wherein said main body includes a first ring-like structure to which said first dilator fingers are hinged and said actuator comprises a second ring-like structure which pivots inside said first ring-like structure, said first and second ring-like structures defining a window through which said cavity can be viewed when said actuator is pivoted into abutment with said first dilator fingers.

7. The speculum according to claim 6 further including a second dilator finger located between adjacent first dilator fingers, said second dilator finger having a proximal end attached to said actuator, a distal end spaced from said proximal end, and opposite lateral edges extending between said proximal end and said distal end, said distal end of said second dilator finger extending beyond said distal end of said first dilator fingers.

8. The speculum according to claim 7 further including a third dilator finger coupled to said main body and located between adjacent first dilator fingers opposite said second dilator finger, said third dilator finger having a distal end that extends beyond said distal end of said first dilator fingers and said distal end of said second dilator finger.

9. The speculum according to claim 8 wherein said third dilator finger is coupled by an integral hinge to said main body.

10. The speculum according to claim 9 wherein said actuator pivots through a first angle prior to abutment with said first dilator fingers so that said second finger commences to move before said first dilator fingers.

11. The speculum according to claim 10 further including a releasable locking mechanism for locking said fingers in a desired juxtaposition and subsequently releasing said fingers.

12. The speculum according to claim 11 wherein said releasable locking mechanism includes a first component provided on said actuator and a second component provided on said main body, said first and second components arranged to engage each other when said actuator is pushed in a direction of insertion of said speculum into said body cavity, and released from each other when a force is applied to said actuator to a direction oblique to said direction of insertion.

13. The speculum according to claim 12 wherein said first component comprises one of a pawl and a rack of teeth-like projections, and the second component comprises the other of the pawl and the rack, said pawl and rack being biased into engagement when said actuator is pushed in said direction of insertion, and lifted apart to effect disengagement when said force is applied.

* * * * *

UNITED STATES PATENT AND TRADEMARK OFFICE
CERTIFICATE OF CORRECTION

PATENT NO.      : 6,287,251 B1
DATED           : September 11, 2001
INVENTOR(S)     : Eric Gay Chee Tan It is certified that error appears in the above-identified patent and that said Letters Patent is hereby corrected as shown below:

<u>Title page,</u>
Item [75], Inventor, change "Gary" to -- Eric --
Item [56], U.S. PATENT DOCUMENTS, change "Barlett" to -- Bartlett --
*Assistant Examiner*– change "Edvando" to -- Eduardo --

<u>Column 1,</u>
Line 24, after "handles" change "arc" to -- are --

<u>Column 5,</u>
Line 31, before "to collapse" change "liners" to -- fingers --
Line 36, before "instrumented" change "Or" to -- or --

Signed and Sealed this

Eleventh Day of March, 2003

JAMES E. ROGAN
*Director of the United States Patent and Trademark Office*